(12) United States Patent
Ravishankar et al.

(10) Patent No.: US 10,490,049 B2
(45) Date of Patent: *Nov. 26, 2019

(54) SYSTEMS AND METHODS FOR IDENTIFYING PATIENT DISTRESS

(71) Applicant: General Electric Company, Schenectady, NY (US)

(72) Inventors: Hariharan Ravishankar, Bangalore (IN); Sahika Genc, Jr., Niskayuna, NY (US); Renjith S. Nair, Bangalore (IN)

(73) Assignee: General Electric Company, Schenectady, NY (US)

( * ) Notice: Subject to any disclaimer, the term of this patent is extended or adjusted under 35 U.S.C. 154(b) by 99 days.

This patent is subject to a terminal disclaimer.

(21) Appl. No.: 14/989,233

(22) Filed: Jan. 6, 2016

(65) Prior Publication Data
US 2016/0192848 A1    Jul. 7, 2016

Related U.S. Application Data

(63) Continuation-in-part of application No. 14/101,663, filed on Dec. 10, 2013, now Pat. No. 9,750,463.

(51) Int. Cl.
*G08B 21/02*    (2006.01)
*A61B 5/0205*    (2006.01)
(Continued)

(52) U.S. Cl.
CPC .......... *G08B 21/02* (2013.01); *A61B 5/02055* (2013.01); *A61B 5/0816* (2013.01);
(Continued)

(58) Field of Classification Search
CPC combination set(s) only.
See application file for complete search history.

(56) References Cited

U.S. PATENT DOCUMENTS 8,190,223 B2    5/2012    Al-Ali et al.
8,911,377 B2    12/2014    Al-Ali
(Continued)

FOREIGN PATENT DOCUMENTS

WO    2015078710 A1    6/2015

OTHER PUBLICATIONS

Charbonnier, Sylvie. "On line extraction of temporal episodes from ICU high-frequency data: a visual support for signal interpretation." Computer methods and programs in biomedicine 78.2 (2005): 115-132. (Charbonnier).*

(Continued)

*Primary Examiner* — Christian Jang
*Assistant Examiner* — Mitchell E Alter
(74) *Attorney, Agent, or Firm* — Andrus Intellectual Property Law, LLP

(57) ABSTRACT

A method includes receiving a first patient data and a second patient data for a time period, wherein the first patient data and the second patient data are measured from a patient. Further, the method includes identifying a plurality of segmented trends in the first patient data and the second patient data as one of an uptrend, a downtrend, and neutral. Furthermore, the method includes classifying at least one segmented trend from the plurality of segmented trends as a pattern. Additionally, the method includes triggering an alarm as an early warning of patient distress based on the pattern.

6 Claims, 12 Drawing Sheets

(51) Int. Cl.
| | |
|---|---|
| A61B 5/00 | (2006.01) |
| A61B 5/08 | (2006.01) |
| G16H 50/20 | (2018.01) |
| A61B 5/0464 | (2006.01) |
| A61B 5/01 | (2006.01) |
| A61B 5/021 | (2006.01) |
| A61B 5/024 | (2006.01) |
| A61B 5/083 | (2006.01) |
| A61B 5/145 | (2006.01) |
| A61B 5/20 | (2006.01) |
| G16H 50/30 | (2018.01) |

(52) U.S. Cl.
CPC .......... *A61B 5/7203* (2013.01); *A61B 5/7275* (2013.01); *G16H 50/20* (2018.01); *A61B 5/002* (2013.01); *A61B 5/0022* (2013.01); *A61B 5/01* (2013.01); *A61B 5/021* (2013.01); *A61B 5/024* (2013.01); *A61B 5/0205* (2013.01); *A61B 5/0464* (2013.01); *A61B 5/0836* (2013.01); *A61B 5/14532* (2013.01); *A61B 5/14542* (2013.01); *A61B 5/201* (2013.01); *A61B 5/202* (2013.01); *A61B 5/7246* (2013.01); *A61B 5/7264* (2013.01); *A61B 5/746* (2013.01); *G16H 50/30* (2018.01)

(56) References Cited

U.S. PATENT DOCUMENTS

| | | | |
|---|---|---|---|
| 8,932,217 | B2 | 1/2015 | Gibson et al. |
| 2010/0113909 | A1* | 5/2010 | Batchelder ......... A61B 5/14551 600/364 |
| 2010/0305412 | A1 | 12/2010 | Darrah et al. |
| 2011/0275910 | A1* | 11/2011 | Amos ................ A61B 5/02416 600/301 |
| 2011/0298621 | A1 | 12/2011 | Shanbhag |
| 2012/0078528 | A1 | 3/2012 | Avinash et al. |
| 2013/0060110 | A1* | 3/2013 | Lynn ...................... A61B 7/003 600/324 |
| 2015/0145691 | A1 | 5/2015 | Eshelman et al. |
| 2015/0157275 | A1 | 6/2015 | Swamy et al. |

OTHER PUBLICATIONS

Bade et al., "Connecting Time-Oriented Data and Information to a Coherent Interactive Visualization", CHI 2004 Proceedings of the SIGCHI Conference on Human Factors in Computing Systems, vol. 6, No. 1, Apr. 24-29, 2004, Vienna, Austria, pp. 105-112.
GE Medical systems Information Technologies, "Dash® 3000/4000/5000 Patient Monitor User Manual", May 10, 2005, 310 Pages.
Ridley, "Common Cause Special Cause Vital Signs Charts", Technology Management for the Global Future, 2006. PICMET 2006, vol. 4, Jul. 2006, pp. 1925-1930.
Zillner et al., "Semantic Visualization of Patient Information", 21st IEEE International Symposium on Computer-Based Medical Systems, Jun. 17-19, 2008, pp. 296-301.
Lehmann et al., "Practical Visualization of Multivariate Time Series Data in a Neonatal ICU", IEEE VisWeek Workshop on Visual Analytics in Health Care, 2010, 4 Pages.
Lynn et al., "Patterns of unexpected in-hospital deaths: a root cause analysis", Patient safety in Surgery, 5(1):3, 2011, 25 Pages.
Aigner et al.,"Comparative Evaluation of an Interactive Time-Series Visualization that Combines Quantitative Data with Qualitative Abstractions", Computer Graphics Forum, vol. 31, Issue: 3, Jun. 2012, pp. 995-1004.
Ma et al., "Integrated Control Chart for Vital Signs Early Warning of Long-Term Care Patients", Ubi-Media Computing and Workshops (UMEDIA), 2014 7th International Conference on, Jul. 12-14, 2014, Ulaanbaatar, pp. 313-318.
Drager, "Infinity® Acute Care System patient monitoring solution", retrieved from "http://www.draeger.com/sites/assets/PublishingImages/Products/mon_infinity_acute_care_system/US/ProductInformation/9068959_IACS_VG3_Insert_PI_US_140822_fin.pdf" on Dec. 10, 2015, 8 Pages.
Welch Allyn, "Propaq® CS Vital Signs Monitor", retrieved from "http://intl.welchallyn.com/documents/PatientMonitoring/Continuous Monitoring/Propaq CS/SM4045-Propaq-CS-Spec-Brochure.pdf" on Dec. 10, 2015, 4 Pages.
Philips, "IntelliVue Patient Monitor", MP20/30, MP40/50, MP60/70/80/90, Patient Monitoring, 2008, retrieved from "http://www.mc.vanderbilt.edu/documents/nursingeducationresources/files/MP20-MP90 Instructions for Use Manual Rev_G_0 English M8000-9001K.pdf" on Dec. 10, 2015, 496 Pages.
Welch Allyn Advancing Frontline Care, "Welch Allyn Connex® Vital Signs Monitor 6000 Series", 2012, retrieved from "http://www.welchallyn.com/content/dam/welchallyn/documents/sap-documents/LIT/80017/80017136LITPDF.pdf" on Dec. 10, 2015,188 Pages.
Philips, "IntelliVue Patient Monitor", MP5/MP5T, Patient Monitoring, 2008, retrieved from http://www.mc.vanderbilt.edu/documents/7north/files/MP5 Rev_ G Training Guide.pdf on Dec. 10, 2015, 90 Pages.
Spacelabs health care, "XPREZZON", 2011, retrieved from "http://www.spacemedical.com.pt/files/XPREZZONcatalogo pesado.pdf" on Dec. 10, 2015, 8 Pages.
Earlysense, Proactive patient care, Retrieved from "Early Detection", http://www.earlysense.com/early-detection/, on Dec. 10, 2015, 3 Pages.
Drews, "Patient Monitors in Critical Care: Lessons for Improvement", Advances in Patient Safety: New Directions and Alternative Approaches (Performance and Tools), vol. No. 3, pp. 1-13, Aug. 2008.

* cited by examiner

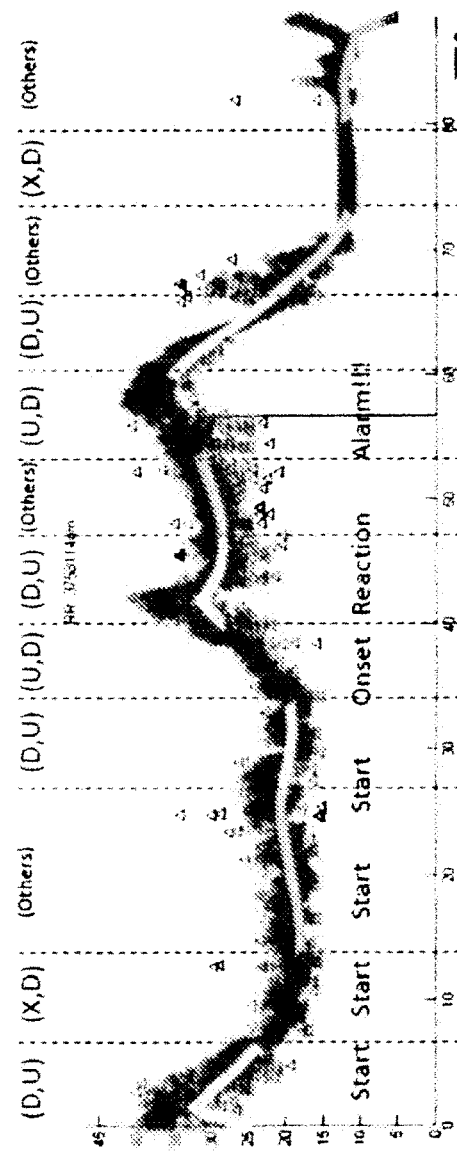
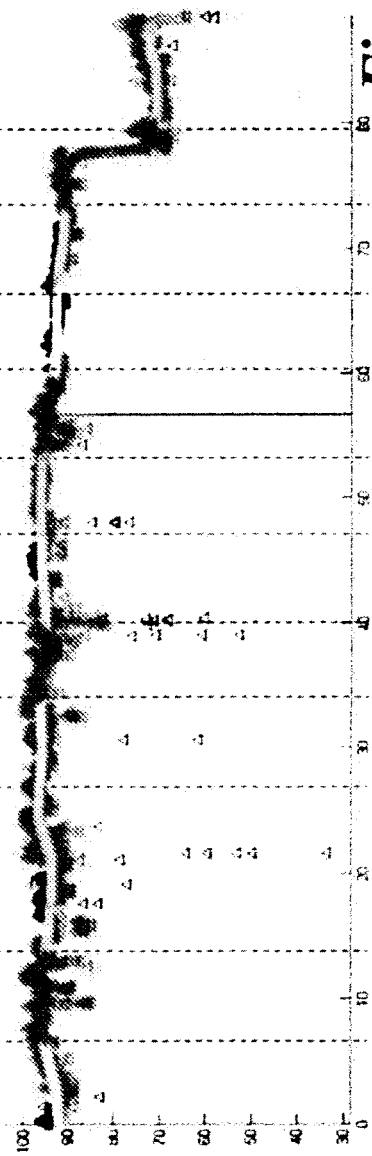
Fig. 4A
Fig. 4B

SYSTEMS AND METHODS FOR IDENTIFYING PATIENT DISTRESS

CROSS-REFERENCE TO RELATED APPLICATIONS

This Application is a continuation-in-part of U.S. patent application Ser. No. 14/101663, entitled "Respiratory stress detection" filed on Dec. 10, 2013, which is herein incorporated in its entirety by reference.

BACKGROUND

The technology disclosed herein generally relates to patient monitoring. More specifically, the technology disclosed herein relates to systems and methods for early identification of patient distress.

Health care professionals such as a clinician, a physician, and the like, measure a plurality of patient data in order to monitor a patient's health. The patient data includes, for example, a blood pressure, a respiratory rate, a blood oxygenation level, a body temperature, an electrocardiogram, and the like. Often, the health care professionals manually analyze the plurality of patient data and determine, for example, whether the patient is in distress or whether the patient's health is improving. In some situations, the health care professionals use patient monitoring systems to monitor the patient's health. However, existing patient monitoring systems have numerous problems. For example, the existing patient monitoring systems fail to identify trends in the plurality of patient data and fail to correlate trends amongst multiple patient data to identify patient distress.

BRIEF DESCRIPTION

In accordance with one aspect of the present specification, a method includes receiving, with at least one processor, a first patient data and a second patient data for a time period, wherein the first patient data and the second patient data are measured from a patient. Further, the method includes identifying, with the at least one processor, a plurality of segmented trends in the first patient data and the second patient data as one of an uptrend, a downtrend, and neutral. Furthermore, the method includes, classifying, with the at least one processor, at least one segmented trend from the plurality of segmented trends as a pattern. Additionally, the method includes triggering, with the at least one processor, an alarm as an early warning of patient distress based on the pattern.

In accordance with another aspect of the present specification, a system is presented. The system includes a plurality of sensors configured to measure a first patient data and a second patient data from a patient for a time period. Further, the system includes a distress detector configured to identify a plurality of segmented trends in the first patient data and the second patient data as one of an uptrend, a downtrend, and neutral. The distress detector is further configured to classify at least one segmented trend from the plurality of segmented trends as a pattern. The distress detector is also configured to trigger an alarm as an early warning of patient distress based on the pattern.

DRAWINGS

These and other features, aspects, and advantages of the present invention will become better understood when the following detailed description is read with reference to the accompanying drawings in which like characters represent like parts throughout the drawings, wherein:

FIGS. 4A-4B depict the classification of the trends into its constituent components, in accordance with one embodiment;

Figure 9:
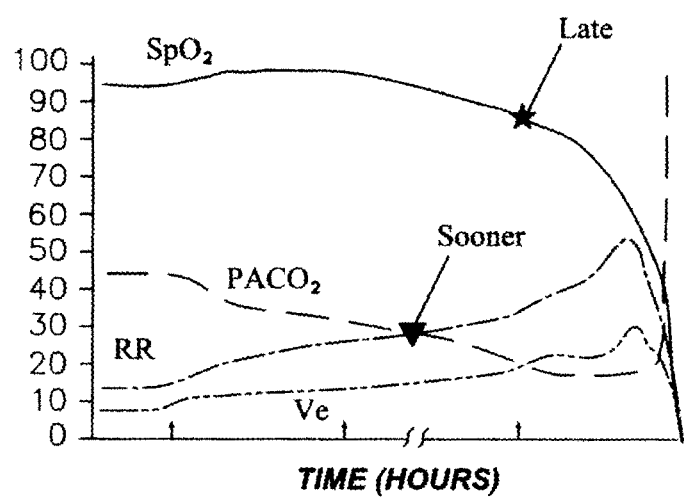
Figure 10:
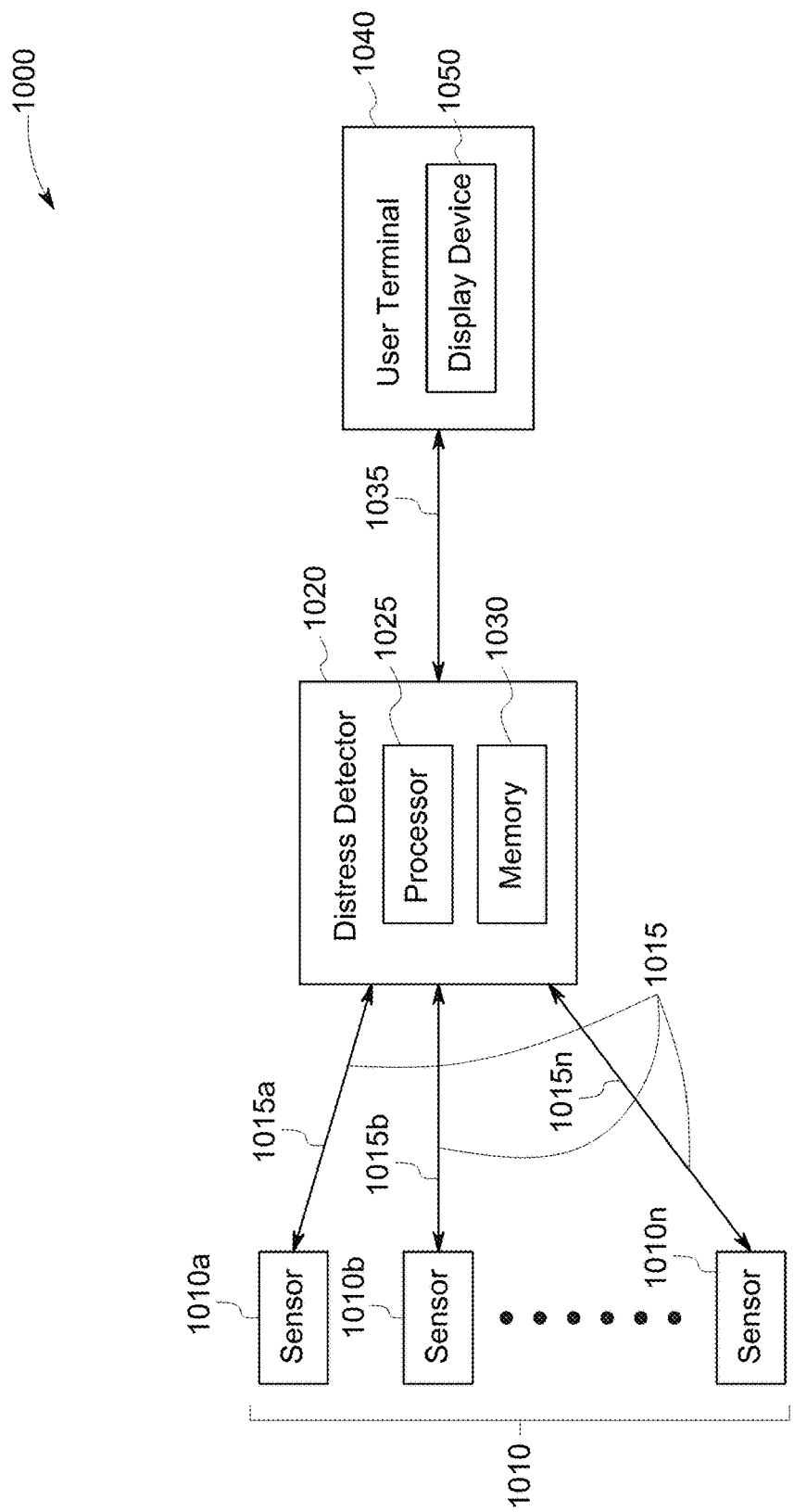
Figure 11:
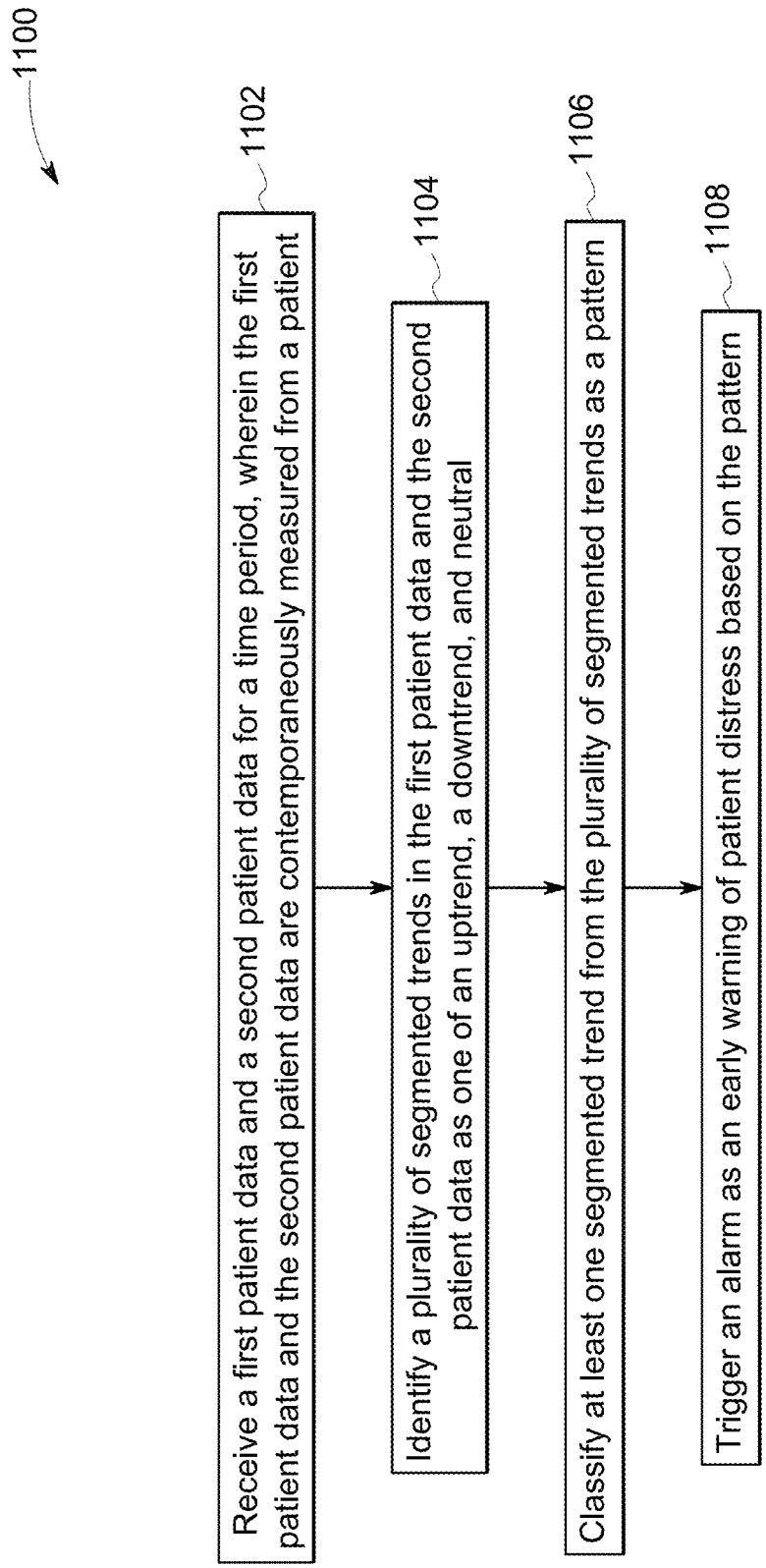
Figure 12:
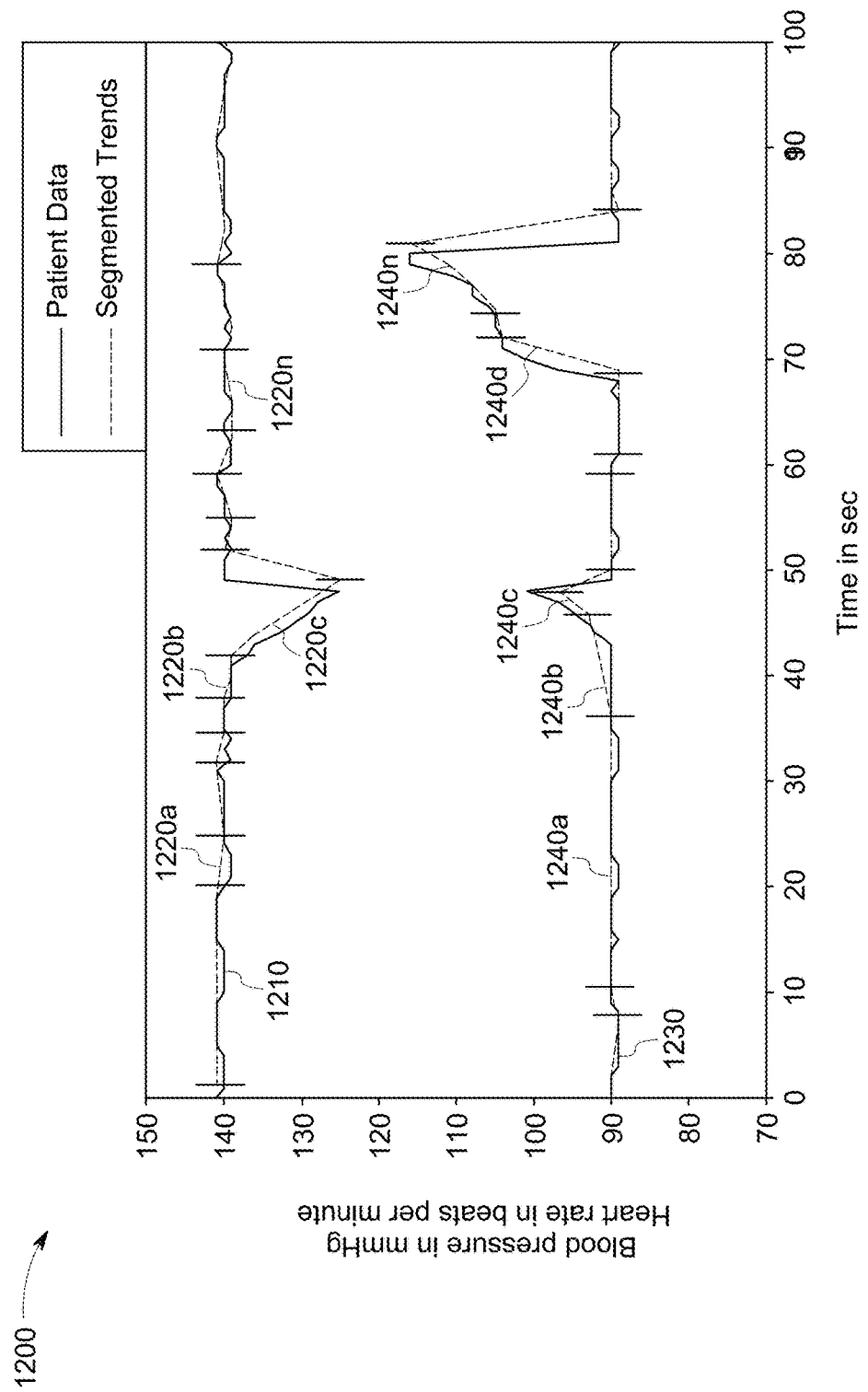

FIG. 9 demonstrates the early indication of distress in one embodiment where $PACO_2$ and RR intersect;

FIG. 10 is a block diagram illustrating an exemplary system for identification of patient distress, in accordance with aspects of the present specification;

FIG. 11 is a flow diagram illustrating an exemplary method for identification of patient distress, in accordance with aspects of the present specification; and FIG. 12 is a pictorial representation of a graph illustrating a heart rate and a blood pressure of a patient in accordance with aspects of the present specification.

DETAILED DESCRIPTION

In the following specification and the claims, reference will be made to a number of terms, which shall be defined to have the following meanings.

The singular forms "a," "an," and "the" include plural references unless the context clearly dictates otherwise.

As used herein, the term "non-transitory computer-readable media" is intended to be representative of any tangible computer-based device implemented in any method or technology for short-term and/or long-term storage of information, such as, computer-readable instructions, data structures, program modules and sub-modules, or other data in any device. Therefore, methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and non-volatile media, and removable and non-removable media such as a firmware, physical and virtual storage, a compact disc read only memory, a digital versatile disc, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein throughout the specification.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Embodiments are directed to systems and methods of utilizing detection methodologies to identify anomalous observations as based on statistical patterns in collected data to recognize patient distress and trigger an alarm at an early stage of distress.

In accordance with aspects of the present specification, an algorithm is described to be utilized with systems to detect respiratory rate and $SpO_2$ so that the system quickly identifies the three types of trend patterns based on an analysis of the respiration rate and $SpO_2$ time series. In addition, the algorithm is extended to recognize and detect other instances of respiratory distress by learning prior patterns of patient instability.

Method

For exemplary purposes, and not limitation, two different methods to tackle the problem of early detection of respiratory distress are characterized. In the first method, a trending algorithm captures the trends in the $SpO_2$ and RR waveforms. Based on the trend estimates, a scheme is utilized to identify trend patterns which are likely to be an early indicator of patient distress. Each trend pattern identified closely mirrors a pattern as one of:

Type I: Hyperventilation Compensated Respiratory Distress (e.g. Sepsis, PE, CHF)—gradual decrease in $SpO_2$ with compensatory hyperventilation.

Type II: Progressive unidirectional hypoventilation—progressive fall in minute ventilation and $SpO_2$, most often brought about my narcotic (sedative) overdose.

Type III: Sentinel rapid airflow/$SpO_2$ reductions followed by precipitous $SpO_2$ fall—This type of pattern is most often noted in patients with sleep apnea wherein breathing is characterized by alternating patterns of hyperventilation and no breath. Death in most instances is a result of arousal failure after a prolonged apnea.

In another approach, a learning algorithm automatically identifies uptrends, downtrends and flat-trends (neutral, or no change) in the $SpO_2$ and RR time series. This information then is integrated into a model to predict the onset of respiratory distress. Further detail of the systems and methods are described in detail in the following subsections.

Model Based Pattern Recognition

In order to accurately estimate the trends in the $SpO_2$ and RR waveforms, a locally weighted least squares fitting algorithm is used which incorporates an outlier rejection step using criteria as stated in the algorithm that follows:

Given a point $x_i$ and its neighborhood estimate (as associated with x variables within a certain time period), an m-order least squares fit by minimizing the following penalty function is utilized:

$$C(\beta_0, \ldots, \beta_n, \lambda) = \sum_{k=1,n} w_k(y_k - \beta_0 - \beta_1 x_k \ldots - \beta_m x_k^m) + \lambda \sum_{k=2,n} |y_k - y_{k-1}|^2$$

where, $y_k$ is the current estimate of the parameter and $x_k$ is the time instance. As compared to the traditional least squares fit, the LOESS method includes an extra penalty term that results in a normalized solution. The choice of the parameter lamda ($\lambda$) and the degree of the polynomial m are instrumental in deciding the smoothness of the generated fit. The variables $w_k$ represent a weighting function and could be appropriately chosen to minimize the influence of outliers.

Figure 1:
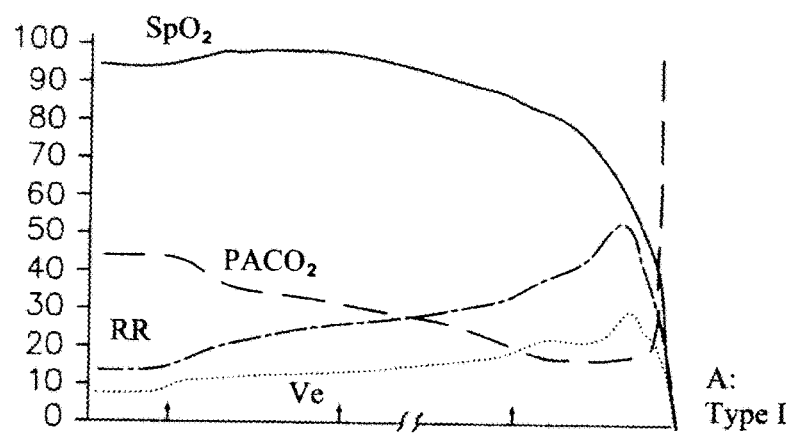
FIG. 1 (PRIOR ART) depicts graphical interpretations of respiratory distress preceding unexplained hospital deaths.
Figure 1:
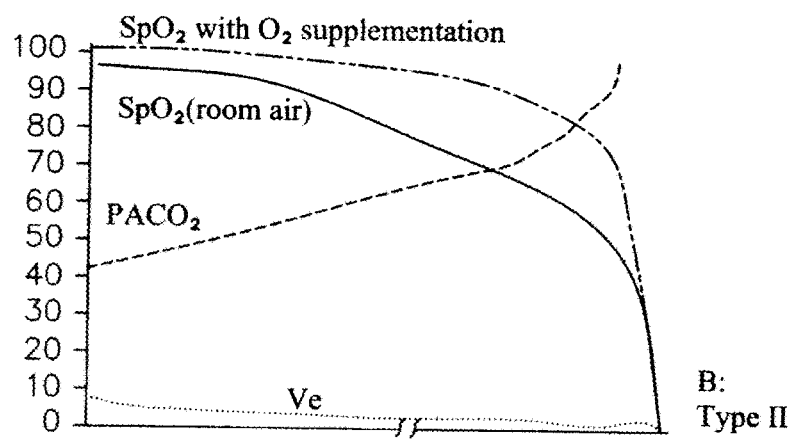
Figure 1:
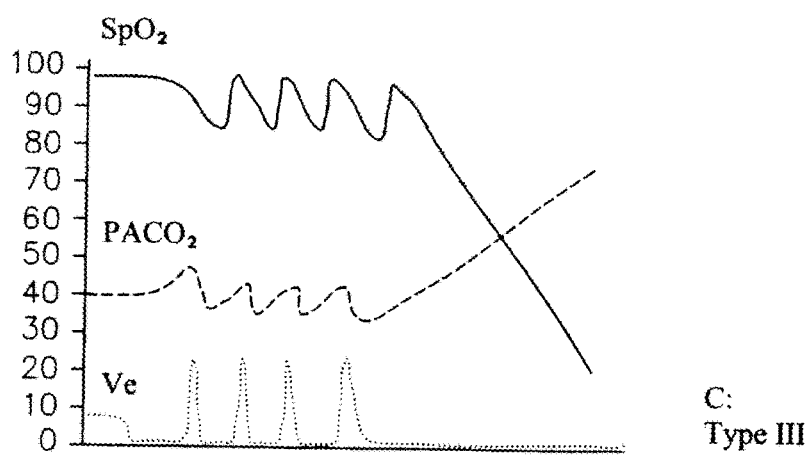
Figure 2A:
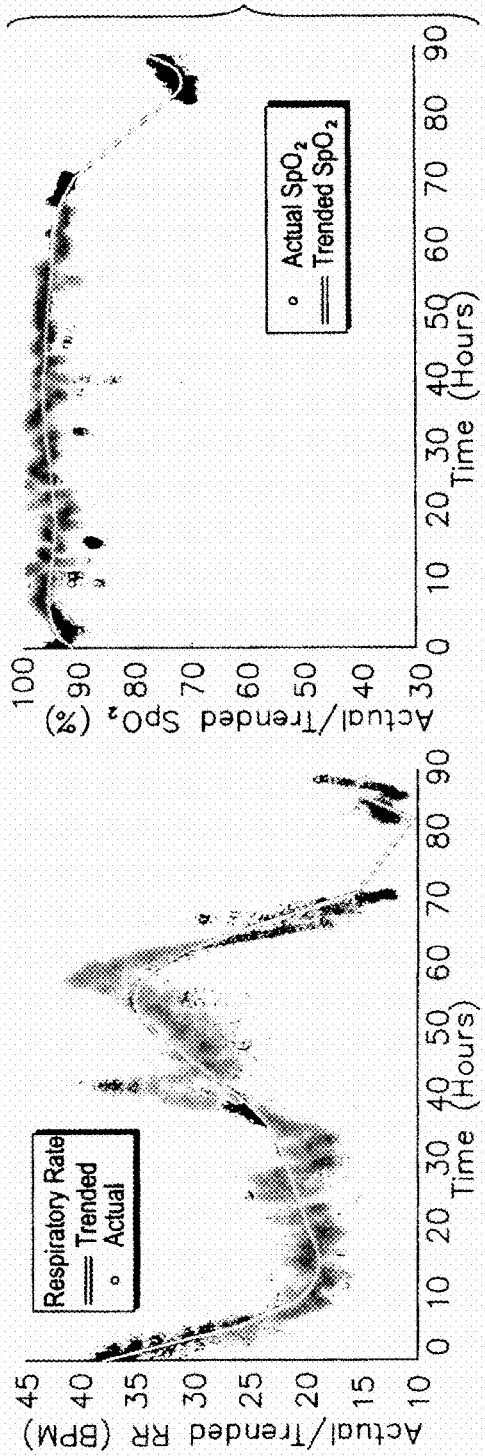
FIGS. 2A-2B depict examples of trend estimates using the proposed algorithm, in accordance with one embodiment.
Figure 2B:
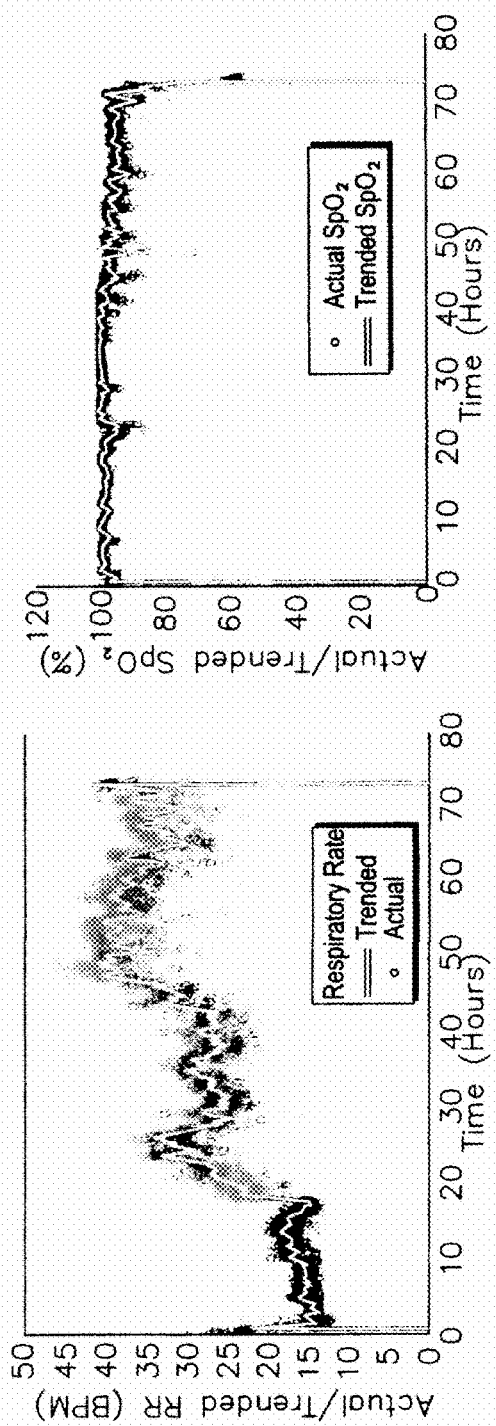

Examples of trend estimates using the proposed algorithm are shown in FIGS. 2A-2B. As illustrated, the left graph in FIG. 2A designates RR rate data points (o) for a patient over a time period of 90 hours, with corresponding trends in $SpO_2$ on the right. In FIG. 2B, the generated trend in RR (indicated by the solid line) for another patient corresponds with the simultaneous recording of $SpO_2$ data points and trends estimated in the graph on the bottom right.

Figure 3:
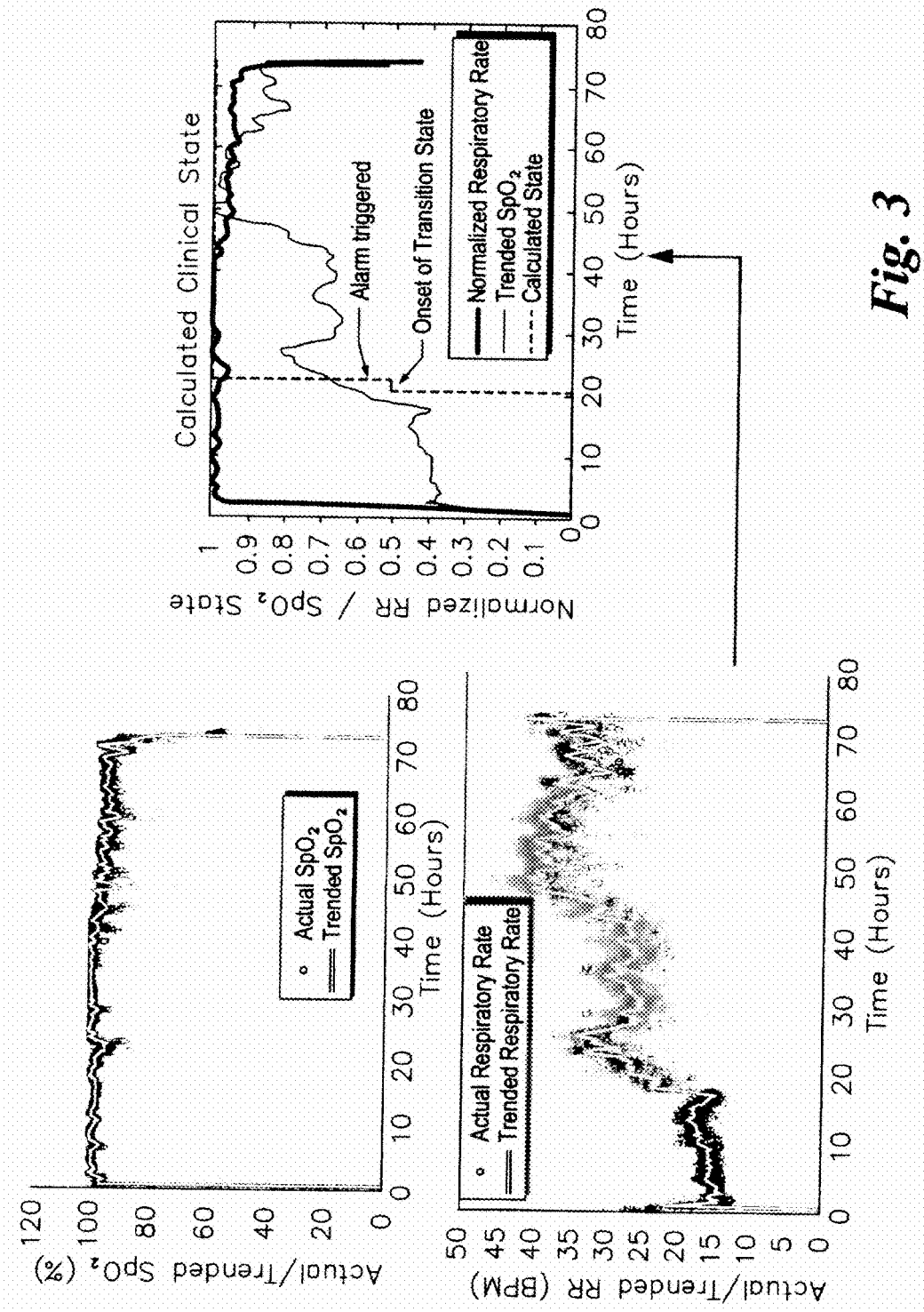
FIG. 3 depicts an aspect of the invention in one embodiment utilizing the Type-1 pattern recognition that triggers a transition state: $SpO_2$ and RR trends are identified to calculate a patient's critical state.

Based on the generated trends, an embodiment of the system identifies each of the three types of patterns (Type I, II, and III) of respiratory distress. An example of Type-1 pattern detection is illustrated in FIG. 3. The Type-I pattern uses an algorithm that looks for a rise in RR rate with a concurrent fall in $SpO_2$. As shown in FIG. 3, as the RR rate rises and $SpO_2$ begins to fall, a transition state is triggered (around about 20 hours). On continuation of this pattern for a preset time, an alarm is triggered around about 23 hours indicating developing patient distress. It is recognized that both the RR rate and $SpO_2$ may not have risen or fallen enough, respectively, to trigger their individual alarms. Thus, the method identifies the interplay between these physiological parameters and gives an early indication of patient distress. Since the trend generation algorithm is agnostic to outliers, noisy deviations of RR and $SpO_2$ estimates are overlooked and therefore largely overcomes the problem of alarm fatigue due to noisy measurements.

In another embodiment, Type II pattern detection follows a similar logic such that the algorithm searches for a gradual downtrend in RR with a concurrent fall in $SpO_2$. As compared to Type I and Type II patterns, the Type III pattern of respiratory distress follows a cyclical pattern of apnea, hyperventilation, apnea, hyperventilation...and so on. An advanced signal processing algorithm is developed to detect these respiratory arrhythmias.

Embodiments of the invention employ the regression algorithm as described coupled with an outlier rejection scheme to accurately estimate trends in RR and $SpO_2$ waveforms. The trends in the waveforms are then utilized in detecting multi-parametric patterns of progressing patient instability.

Trend Classification and State Space Method

In the previous embodiment, a method for early detection of respiratory distress utilized trend analysis of RR and SpO2 waveforms. In one aspect, the method is based on a modeling principle involving detection of prior patterns in these trends. In another embodiment, the approach is utilized to detect respiratory distress in cases where these prior patterns (Types I, II, and III) may not manifest. The embodiment learns variable patterns of respiratory distress based on previous learning examples.

Prior to learning patterns of respiratory distress, the trend is decomposed into its constituent components for further analysis. Trend components primarily comprise an 'uptrend', 'downtrend' and 'neutral'. Further classification is also possible based on classifying the uptrend or downtrend into mild or severe categories. Subsequent to decomposing the trend into its constituent components, the system proceeds to utilize the information in a Hidden Markov Model (HMM) framework for early prediction of respiratory distress. In the HMM framework, the state is not directly visible; but output, dependent on the state, is visible. Each state has a probability of distribution over the possible outputs (i.e. The process itself cannot be observed, and only the sequence of events or measurements can be observed and recorded). Therefore the sequence of outputs generated by the HMM gives some information about the sequence of states. The steps are explained as follows:

A. Trend Classification

Given a trend, the goal is to classify the portions of the trend into one of three categories 'uptrend', 'downtrend' and 'neutral', constituent components of the overall trending in accordance with one embodiment. Exemplary classifications are illustrated in FIGS. 4A-4B where each segmented portion of the trend denotes an uptrend, a downtrend, a neutral, or alarm. These classifications in the algorithm allow for trend segmentation and analyzing the segmented trends within the linear approximation algorithm.

As depicted in FIG. 4A and FIG 4B, the identified patterns are identified by segmented lines, but typically designated in color codes to highlight various local events that are helpful in detecting distress. Here, for example, Type-1 respiratory distress is recognized. The top plot in FIG. 4A is the respiration rate for a patient in breaths per minute over time in hours and the bottom plot in FIG. 4B is the corresponding oxygen saturation for the patient in percentage over time in hours. In one embodiment, for example and not limitation, the color code is as follows:

Red—Simultaneous increase in RR and decrease in $SpO_2$ (principal indicator of Type 1 pattern)
Yellow—Simultaneous decrease in RR and increase in $SpO_2$
Black—Decrease in $SpO_2$ irrespective of the change in RR (when the above two conditions are not met)
Purple—Increase in RR irrespective of the change in $SpO_2$ (when the above conditions are not met)
Green—when none of the above conditions are met—No useful event.

Detection of these events using the trend segment classification approach is explained as follows. Each trend segment of FIG. 4B corresponds to each trend that is classified in FIG. 4A and classified as stable (X), up (U), and down (D), and obey the following rules:

Piecewise Linear Approximation: After dividing the trend waveforms into segments, the line segments are fit over the trended RR and $SpO_2$ values observed within the window under consideration. The slope of the line segments is used to classify them into one of the— stable, increase (up) or decrease (down) classes.

Since this classification is purely algorithm driven and not based on manual annotation (See FIGS. 8A-8B: manual annotation by clinicians), the classification result of the segment may not match suitably with the visual inference. This happens mainly in cases where the change in RR or $SpO_2$ is too small to decipher precisely.

Where the RR or $SpO_2$ values change significantly over the window, the classification may not capture the dynamics properly. This is due to the fact that the classification is based on the properties of the 'line segment' (a line of best-fit); it does not have the capability to capture all higher order variations within the segment.

As illustrated in FIG. 4A and FIG 4B, an alarm is triggered when a Type I pattern is recognized. The system 400 is configured to trigger alarms at designated events that are pre-determined patterns or unstable patterns recognized by the algorithm. Specifically, the segmented trends that are better visualized in a color schematic assist the system in identifying patterns early and preventing false alarms. The configuration of the system as mentioned is designed with a micro-analytic focus so that individual segmented trends are identified by the linear approximation as opposed to taking an overall trending visual. Thus, the Drawings disclosed herein have intended to segment the trending line as based on localized data points screening out localized noise and extraneous data in real-time.

Figure 5A:
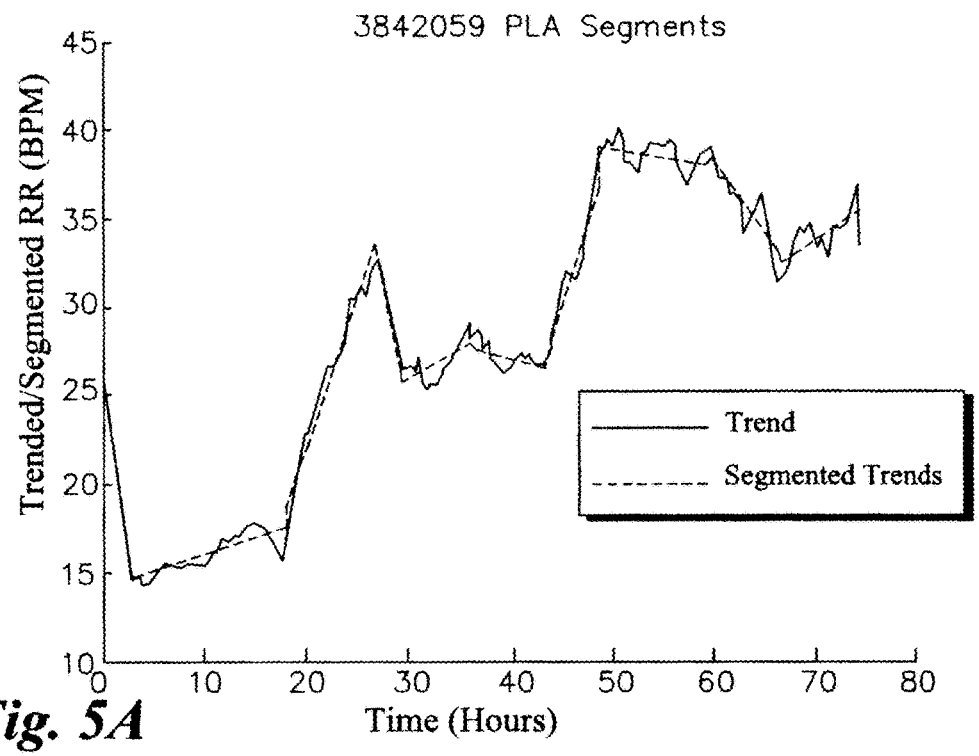
FIGS. 5A-5B illustrate a learning methodology for trend segmentation, in accordance with embodiments of the invention.
Figure 5B:
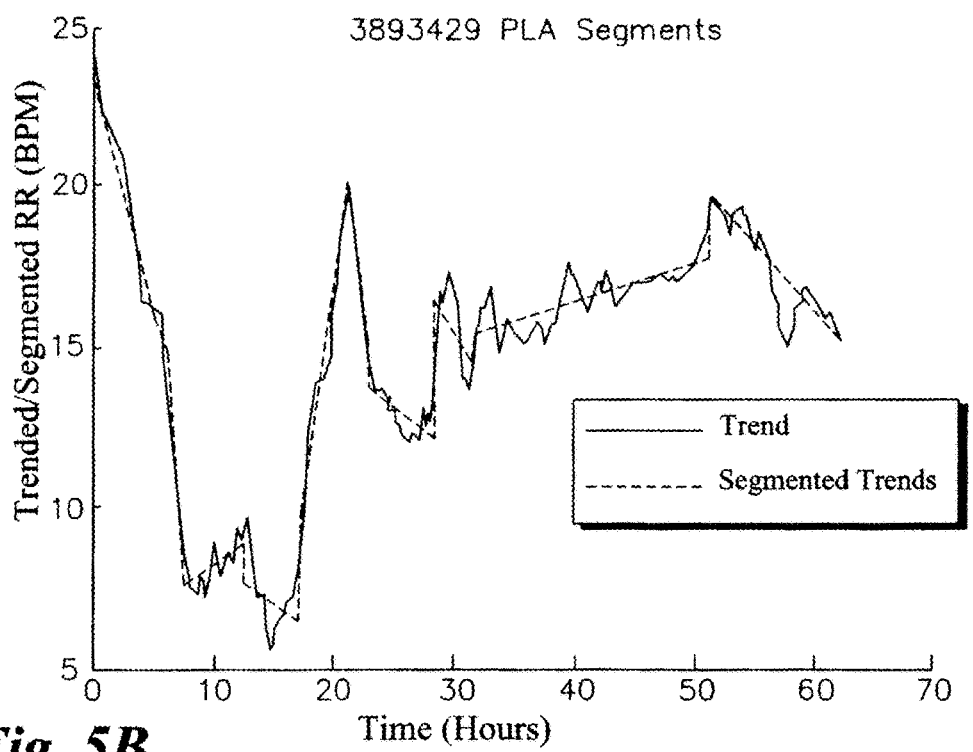

FIGS. 5A-5B illustrate a learning methodology for trend segmentation, in accordance with one embodiment. Trends associated with the learning examples in one embodiment are then decomposed into linear segments using the piecewise linear approximation (PLA) algorithm. As depicted, FIG. 5A and FIG. 5B, respectively, each demonstrate trend segmentation as determined by identifying and minimizing outliers while separately characterizing the trend using a linear regression model. FIG. 5A corresponds to data from a first patient; FIG. 5B corresponds to data from a second patient.

Aspects of the method are explained in the following steps:

1) The trends in RR and SpO2 are manually annotated to create a database of learning examples.
2) The trends associated with the learning examples are then decomposed into linear segments using the piecewise linear approximation (PLA) algorithm. Examples of PLA output are shown in FIGS. 5A-5B. As illustrated, the trend lines are depicted in solid trending segments and the PLA as a dashed line.
3) The linear PLA segments are then input as feature vectors into a decision tree learning algorithm.
4) When a new dataset is encountered (outside of training examples) it is passed through the learned decision tree network to automatically generate the segmented trend.

B. State Space Method

Based on the trend classification in one embodiment, each trend is represented by a 3-tuple time series T: {TY, t, s} where TY denotes uptrend (U), downtrend (D) or neutral (N), t denotes the time duration for which the trend component is active and s denotes the strength (s=0, 1, and 2 for mild, moderate and severe trends respectively) which is representative of the magnitude change in the parameter value over the course of the trend. In one aspect, the trend itself can be characterized by expressing it as T RR/SpO2= [T1, T2 T3 . . . Tn] where the Ti's are the instances of the trend segments as generated by the decision tree algorithm.

An example of such labeling for the trends in FIGS. 4A-4B would be TRR/SpO2=[{U,2, 1}, {D,10,2}, {N,23,0}, {U,16,2}, {D,5,1}, {U,12,2}, {D,13,2}, {N,12,0}]. In this aspect, TRR/SpO2 is referred to as the label vector. The label vector is generated in real-time and is continuously updated as new data comes in. Given the label vector (for both RR and SpO$_2$ trend sequences) as an observation sequence, a state space is defined characterizing an HMM framework for respiratory distress as shown in FIG. 6, also known here as the state space model (SSM) for detecting respiratory distress.

Figure 6:
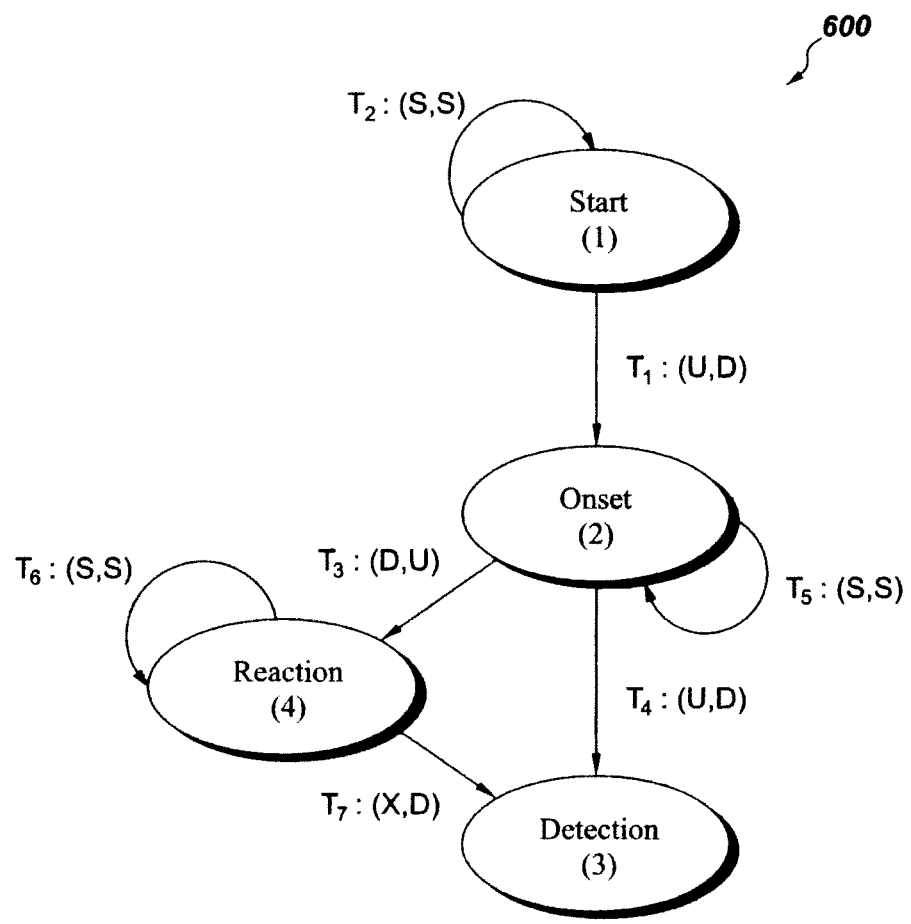
FIG. 6 is a flow diagram in one embodiment as to a state space model for detecting respiratory distress.

In FIG. 6, the flow diagram charts one example of a method of segmenting a digital image, in accordance with one embodiment. A Markov process can be thought of as 'memoryless'; a process satisfies the Markov property if one can make predictions for the future of the process based solely on its present state. In one aspect, one could know the process's full history (i.e., conditional on the present state of the system, its future and past are independent). A Markov process is defined by its set of states, transitions, and events. The Markov process model 600 for Type 1 pattern shown in FIG. 6 comprises four states: (1) "Start", (2) "Onset", (3) "Reaction", and (4) "Detection", which are depicted with circles and state labels inside the circles. Seven transitions include: "$T_1$: Start→Onset", "$T_2$: Start→Start", "$T_3$: Onset→Reaction", "$T_4$: Onset→Detection", "$T_5$: Onset→Onset", "$T_6$: Reaction→Reaction", "$T_7$: Reaction→Detection". Four event labels, "(S, S)", "(U, D)", "(D, U)", "(X, D)", where S, U, and D correspond to stable (S), up (U), and down (D) trends in the time-series signal over a fixed or variable time window, and the first and last letters in the parenthesis separated by a comma correspond to trends in respiration rate and oxygenation, respectively.

The SSM refers to a class of probabilistic graphical models that describe the probabilistic dependence between the latent state variable and the observed measurement. In one aspect, the statistical technique is used to characterize the dynamic features in trending RR and SpO$_2$, also characterized as noisy and temporal.

The parameters of this model are learned using prior training data. Once the model is learned, the most likely state sequence can be predicted using, for instance, the Viterbi back propagation algorithm. The Viterbi algorithm is a dynamic programming algorithm for finding the most likely sequence of hidden states in the context of hidden Markov models. Knowledge of the state sequence enables prediction as to the early onset of respiratory distress.

Results

Prototype versions of an embodiment of the algorithm were tested on a sample dataset of nineteen patients out of which nine patients had respiratory distress while the others did not report any distress. In one aspect, the algorithm accurately determines the onset of respiratory distress in eight out of nine patients with a lead time exceeding 15 hours prior to patient mortality. Thus, the method is able to alert the physician as to a deteriorating patient condition much before the patient undergoes severe health deterioration. In addition, the test on the normal subjects reveals that no alarms are generated for 8 out of 10 patients reflecting a false alarm rate of 20%. Table 1 indicates the early warning capability in one embodiment.

TABLE 1

Early warning capability of an embodiment of the algorithm as utilized on patients who suffered mortality due to respiratory failure.

| File Name | Number of hours patient lived | Time when the alarm was triggered (EARLY ALERT) |
| --- | --- | --- |
| 3167864 nm | 103.56 | 43.35 |
| 3192258 nm | 67.400000 | 30.016667 |
| 3254526 nm | 102.550000 | 43.350000 |
| 3340926 nm | 26.316667 | 0.000000 |
| 3401319 nm | 209.866667 | 30.016667 |
| 3634632 nm | 25.800000 | 16.683333 |
| 3758114 nm | 88.666667 | 43.350000 |
| 3842059 nm | 74.183333 | 43.350000 |
| 3893429 nm | 62.266667 | 30.016667 |

Figure 7:
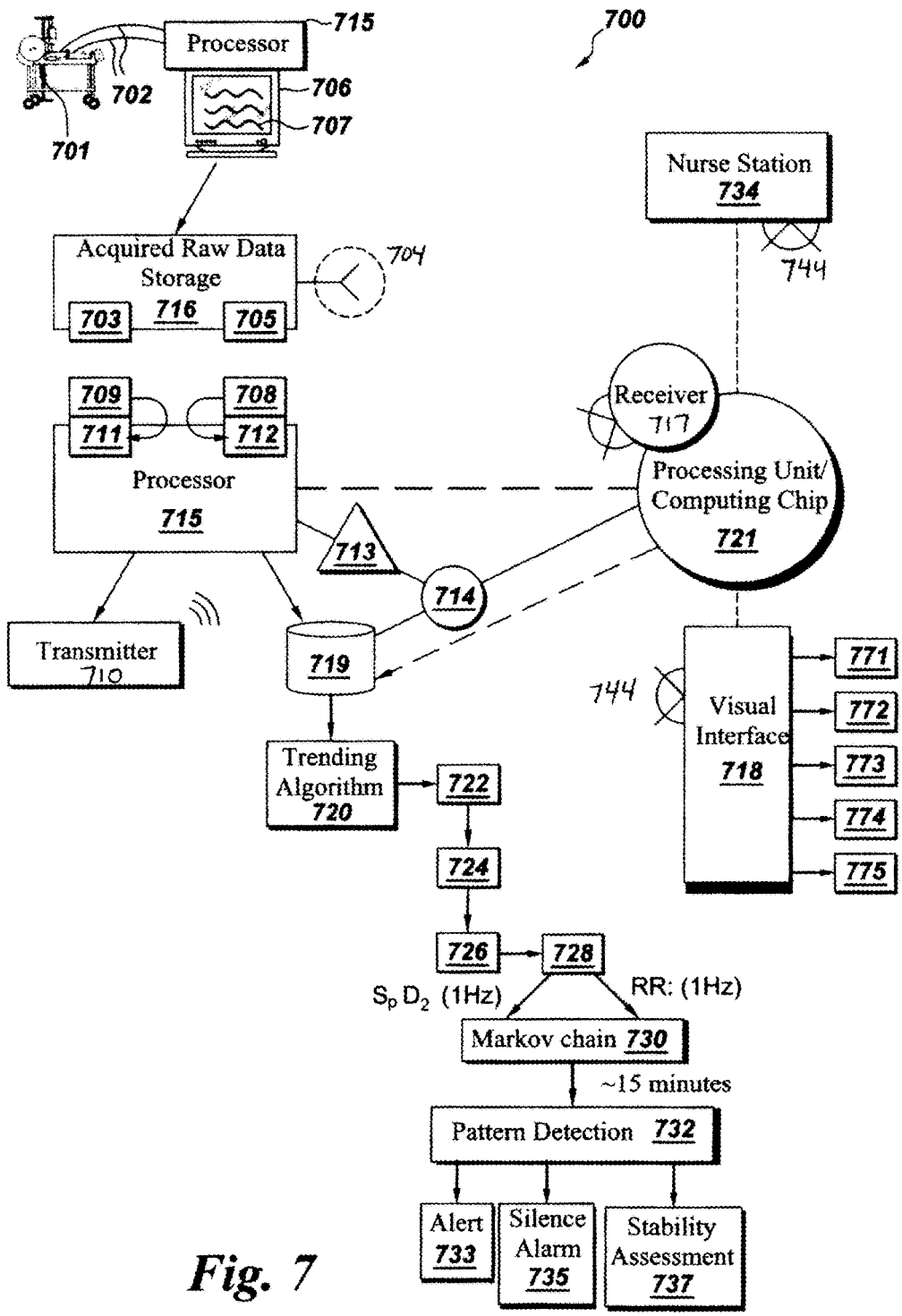
FIG. 7 is a schematic of an example of the system for carrying out one or more embodiments.

As illustrated in FIG. 7, an embodiment of the system 700 is depicted in a schematic. A patient 701 has attached sensors connected by leads 702 to a monitor 706 for monitoring impedance respiration 703 and pulse oximetry 705, the acquired raw data of which is stored in the database 716. Signal quality detection is then optimized: The respiratory rate is extracted by calculating the dominant pulse rate within a specific time frame that includes at least three inhale and exhale periods (e.g., 24 seconds) in the respiration rate form. The dominant pulse rate is calculated from time-frequency representation of the respiration waveform within the specified time frame by determining the frequency components with larger power compared to other frequency components within the admissible respiration rate range (about 5-50 breaths per minute).

From waveform readouts 707 on the monitor 706 from impedance respiration 703, respiratory rate 709 is extracted; from waveform readouts 707 of pulse oximetry 705, oxygen saturation 708 is measured simultaneously. Numerics data from the recording monitors 706 translates respiratory rate 709 as breaths per minute 711. Numerics data from monitors 706 translates oxygen saturation as SpO$_2$ 712 between 0%-100%.

As illustrated, a server 713 is connected to a network 714 within the hospital infrastructure to capture the data for analytics by a processor 715. A database 719 standardizes the information and monitors patient data, on an individualized patient treatment and monitoring protocol.

Aspects of the system 700 allow wireless connectivity 704 of the raw data storage 716 and the database 719 to a network 714 and permit the use of multiple visual interfaces 718, including those such as a television 771, health monitor 772, iPhone 773 or similar device, laptop 774, portable electronics 775, among others. This integration of the system 700 with personal computing devices and portable electronics 775 expands the communication capabilities between clinicians, as well as to facilitate patient observation from remote locations. In one aspect, a processor 715 embedded with Windows® connects to the numeric database processing unit 721 to analyze the data in real-time. In another aspect, the processor 715 is hardwired directly to the database 719.

In one aspect, a transmitter 710 is a separate piece of electronic equipment, or can be an electrical circuit within another electronic device. The receiver 717 as part of the processing unit 721 converts signals into usable information. The receiver 717 and transmitter 710 can also be combined into one unit. The information provided to the transmitter is in the form of an electronic signal, such as an audio (sound) signal from a microphone, a video (TV) signal from a video camera, or in wireless networking 744 a digital signal as from a computer (e.g. devices such as those used as visual or audio interfaces 718 including 771, 772, 773, 774, 775, etc.).

The real-time processor 715 in connection with database 719 has an interface that sees episodic data of lab values, pharmaceutical use, electronic medical records (EMRs), visual and/or clinical notes in combination with the RR and $SpO_2$ data. A trending algorithm 720 is associated with the measurements over a brief period of time between about 2 minutes to about 20 minutes, or even trends realized in less than about a minute. The trends are determined by the sampling rate or as detected over increments of time per individual patient. Characteristics of the signal are defined and any noisy or temporal measures are identified and selected out to more accurately characterize the trend. Averaging data and correlating trends of different parameters can correlate data between parameters as desired. Further averaging and correlating minuscule trends, mini-trends, allows for more specificity and sensitivity in detection and analysis. Irregularity or variance in trending is analyzed during anomaly detection 722. By identifying mini-trends over the course of time, and associating any anomalies, a pattern inquiry 724 identifies a specific pattern. If there is a pattern of interest, pattern classification 726 specifies the type of pattern and is statistically verified in real-time through statistical verification 728. The statistical and temporal properties build and characterize the features that are utilized in pattern recognition; the Markov process model 730 completes the pattern recognition.

In one embodiment, LOESS line of regression is utilized to mark mini-trends during a time period. Once patterns are recognized, the Markov chain 730 is identified such as "down, down, up" for Type I (as illustrated in FIG. 7). Trending may be characterized by Types I, II, or III, but also learned via ongoing patient monitoring as characteristic and unique to a particular patient. For exemplary purposes, and not limitation, in a timeframe of about 15 minutes, patterns are recognized and type identified at pattern detection 732. The detected pattern is then monitored for sensitivity and specificity to alert a clinician as to patient distress 733, silence false alarms 735, or assess a patient's stability 737, among other conditions as specified in the recognition process. Advantageously, the system and method of recognizing critical alarms sooner as to a patient's respiratory distress can be continuous ongoing real-time monitoring without the manual recording of measurements by a clinician. Further, the arbitrary analysis that is based on a clinician's subjectivity is removed so that critical alarms are quickly identified before a patient is in distress. Also, a clinician realizes the severity of an alarm sooner (and less often) so as to remove any mistaken silencing of alarms and more easily monitor multiple patients in a hospital setting.

Figure 8A:
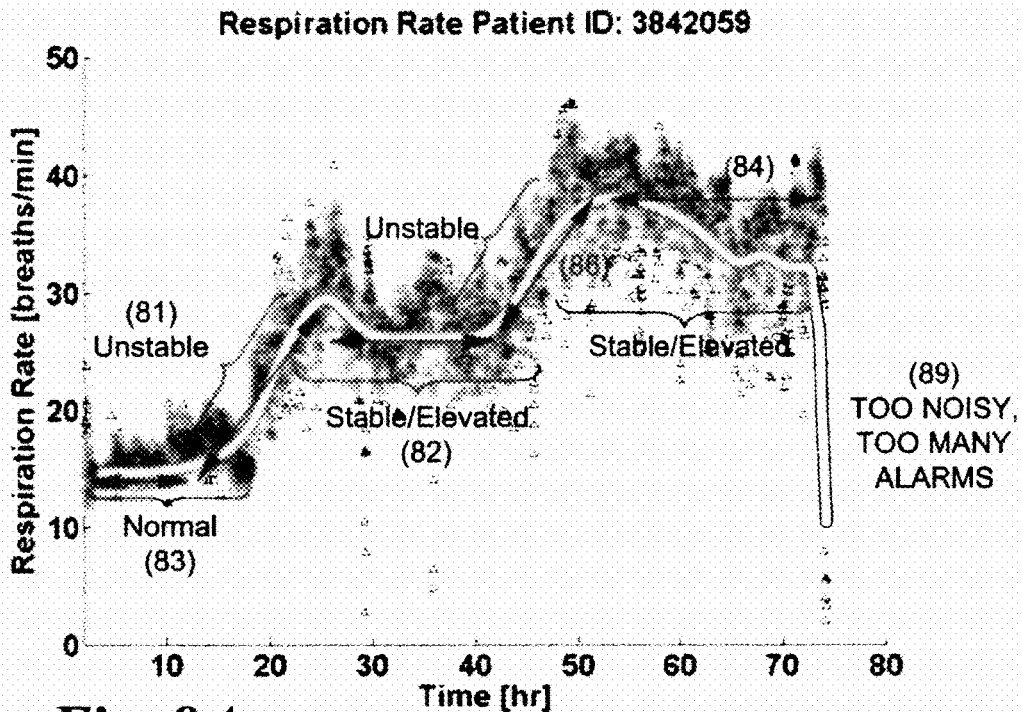
FIG. 8A depicts the use of a system in one embodiment that recognizes patterns in respiratory rate utilizing characterization of trends to address patient stability or instability and prevent overuse of alarms.
Figure 8B:
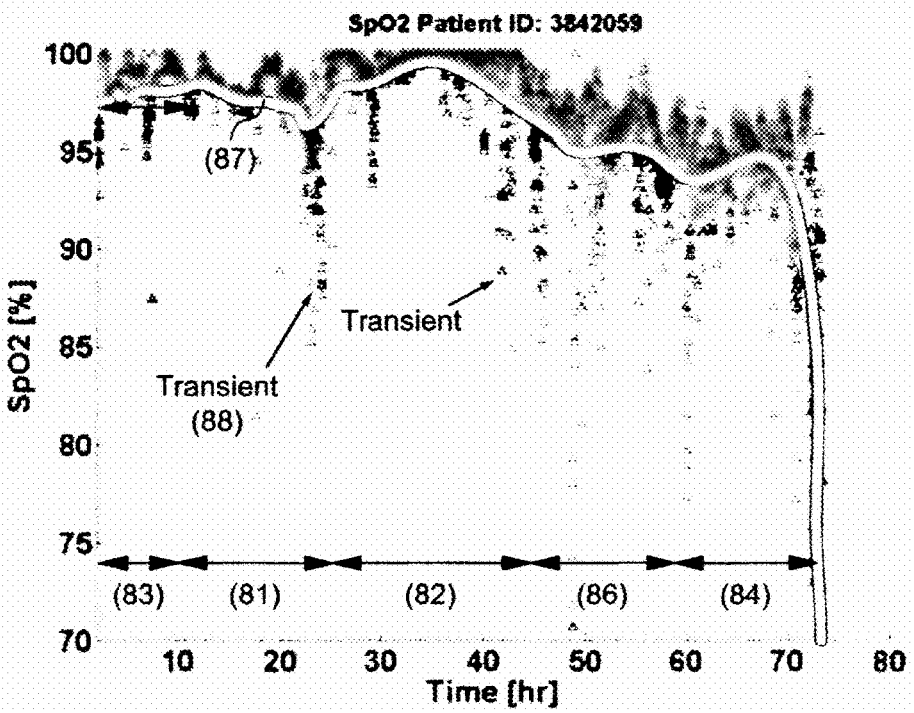
FIG. 8B depicts use of the system as it identifies transient $SpO_2$ indicators and correlates RR in FIG. 8A with the $SpO_2$ trends to prevent delayed response.

Embodiments of the system 700 can provide a service-oriented architecture or processing packages such as computing chips that process the raw data and numeric with trending analysis and pattern recognition to deliver faster, real-time notification of patient states. Where logic is incorporated into a processing chip, executable computer programs integrate the trending algorithms and pattern recognition in real-time and with security protections to protect patient data. Table 2 below shows the monitoring of $SpO_2$ over a time period of hours and the trigger that alerts a clinician automatically based on trended respiratory rate and $SpO_2$ trending. Any transient data is selected out to identify mini-trends in the overall pattern over the selected timeframe. Here, for exemplary purposes, and not limitation, a Patient #1 with an SpO2<90% typically sets off an alarm; with the novel pattern recognition of the invention, Patient #1 is actually in distress at 75 hours as based on correlated respiratory rate and SpO2. FIGS. 8A-8B illustrate the mini-trends, selected out transient data (that which deviates outside the associated trends), and patient state (e.g. normal, unstable, stable, elevated, etc) according to those trends. FIG. 8A depicts a patient's RR recorded; a patient's SpO2 is simultaneously recorded in FIG. 8B. Since the trends in RR and SpO2 are collected simultaneously in real-time, the data is recorded simultaneously and correlated. The corresponding segmented trends are compared and analyzed continuously to recognize a pattern that provides an early alert as to patient distress.

TABLE 2

At least 10 hours early indication with simple anomaly detection (See FIGS. 8A-8B).

| Patient | Current Monitoring - $SpO_2$ < 90% violation occurs at T (hours) | Trigger on trended Resp. & $SpO_2$ occurs at T (hours) |
| --- | --- | --- |
| 1 | 100 | 75 |
| 2 | 65 | 25 |
| 3 | 100 | 67 |
| 4 | N/A | 18 |
| 5 | 180 | 97 |
| 6 | 25 | 15 |
| 7 | 70 | 42 |
| 8 | 70 | 42 |
| 9 | N/A | 25 |

FIGS. 8A-8B illustrate where a clinician manually denotes RR as "Unstable" (81, 86), "Stable/Elevated" (82, 84), or "Normal" (83) to characterize recognized trends that can be identified as a pattern to indicate patient distress. Too many alarms are triggered when the RR trends appear to drop significantly where noisy variation (89) plays a part. FIG. 8B depicts SpO2 trending data (87) with various transient data points (88) that cause at least about 90% persistent violation such that the patient has already deteriorated in condition and it is too late to act. The SpO2 data and trends denoted in FIG. 8B correspond to the simultaneous collection of RR data from the patient of FIG. 8A.

CONCLUSIONS

Overall, embodiments of outlined novel schemes for early detection of respiratory distress have been disclosed. While two varied approaches to respiratory distress detection have been detailed, a synergy between the two allows amalgamation of the two techniques into a singular approach. In one embodiment, the algorithm is refined to improve the false alarm performance as well as to test the algorithm on a more extensive dataset. Furthermore, additional multi-parametric trends are identified, measured, and utilized in the analytics to expand the scope to include fields outside of respiratory distress including early detection of cardiopulmonary arrest, respiratory failure, renal failure, sepsis, and re-intubation risk, among others. To prevent silencing of critical events, the corresponding time series is processed to detect its quality and relevance within context. Descriptors as disclosed include respiratory rate, patient history, $SpO_2$, and vital signs that could also integrate patterning algorithms such as heart rate, electronic sensor monitoring, among others. Overall, non-actionable alarms are reduced to improve the confidence in sensors and machines.

For exemplary purposes only, and not limitation, an embodiment of the system in FIG. 9 illustrates earlier triggering of alarms when patterns are recognized sooner rather than later. This earlier recognition improves clinician response and addresses the inaccuracy of alarm systems. The automatic recognition of trending and patterns in real-time further provides clinical systems with the monitoring and analytical capabilities that prevent false alarm fatigue and alert providers earlier as to deteriorating patient condition. As utilized herein, the system disclosed utilizes a trending algorithm to predict patient stress, particularly respiratory distress, early on. The sooner response (marked by a triangle in FIG. 9) provides early detection and warning by acknowledging simultaneous trending patterns in RR and $SpO_2$; thus, saving a patient from a detrimental occurrence when the late alarm is too late (indicated by a star in FIG. 9) in providing an urgent care response.

Without limitation, patterns of distress using an algorithm of the invention, trending and pattern recognition may utilize data from platelet count, sensor bands, neutrophil count, lymphocyte count, inflammatory markers, temperature, EKG rhythm, pulse rate, pulse variability, pulse upstroke, blood pressure, hemoglobin, $SpO_2$, respiratory rate, ventilation-oximetry, serum potassium, serum bicarbonate, serum sodium, anion gap, serum chloride, urine RBC, serum creatinine, urine WBC, urine output, among other patient data that remain misunderstood in the numbers of unexpected hospital deaths.

Although, the description hereinabove is directed to systems and methods for respiratory distress detection, these systems and methods may also be used for identification of other types of patient distress, such as, but not limited to, ventricular tachycardia, shock, and the like. Such systems and methods may be useful in a hospital setting, an outpatient setting, an ambulatory setting, or combinations thereof. FIG. 10 illustrates a block diagram of an exemplary system 1000 for identification of patient distress, in accordance with aspects of the present specification. In the illustrated embodiment, the system 1000 includes a plurality of sensors 1010a, 1010b, . . . , 1010n (referred to collectively as sensors 1010), a distress detector 1020, and a user terminal 1040. The plurality of sensors 1010a, 1010b, . . . , 1010n are communicatively coupled to the distress detector 1020 via wired signal lines 1015a, 1015b, . . . , 1015n (referred to collectively as wired signal lines 1015) respectively. Similarly, the distress detector 1020 is communicatively coupled to the user terminal 1040 via a wired signal line 1035. Although, in the illustrated embodiment, the plurality of sensors 1010, the distress detector 1020, and the user terminal 1040 are communicatively coupled via wired signal lines 1015 and 1035, in other embodiments, the plurality of sensors 1010, the distress detector 1020, and the user terminal 1040 may be communicatively coupled wirelessly or using a combination of wired and wireless coupling.

The plurality of sensors 1010 may be any type of sensors that are configured to measure a plurality of patient data, for example, respiratory rate, pulse oximetry, blood pressure, heart rate, body temperature, and the like. In one embodiment, the sensors 1010 may be configured to measure a plurality of patient data contemporaneously (i.e., at the same time period). For example, the sensor 1010a and the sensor 1010b may be configured to contemporaneously measure a first patient data (e.g., blood pressure) and a second patient data (e.g., heart rate) of the same patient. The plurality of sensors 1010 may be further configured to send the plurality of patient data to the distress detector 1020 via the signal lines 1015.

The distress detector 1020 may be any type of device that is configured to receive the plurality of patient data and identify patient distress based on the plurality of patient data. In the illustrated embodiment, the distress detector 1020 includes a processor 1025 and a memory 1030. The processor 1025 may include at least one arithmetic logic unit, microprocessor, general purpose controller or other processor arrays configured to perform computations, and/or retrieve data stored in the memory 1030. In one embodiment, the processor 1025 may be a multiple core processor. The processor 1025 processes data signals and may include various computing architectures including a complex instruction set computer (CISC) architecture, a reduced instruction set computer (RISC) architecture, or an architecture implementing a combination of instruction sets. In one embodiment, the processing capability of the processor 1025 may support the retrieval of data and transmission of data. In another embodiment, the processing capability of the processor 1025 may also perform more complex tasks, including various types of feature extraction, modulating, encoding, multiplexing, and the like. In yet another embodiment, the processor 1025 may be similar to the processor 715 and the processing unit 721 as illustrated in the embodiment of FIG. 7. Other type of processors, operating systems, and physical configurations are also envisioned.

The memory 1030 may be a non-transitory storage medium. For example, the memory 1030 may be a dynamic random access memory (DRAM) device, a static random access memory (SRAM) device, flash memory or other memory devices. The memory 1030 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 1030 stores data that is required for the distress detector 1020 to perform associated functions. In one embodiment, the memory 1030 stores codes and routines that are accessible and executable by the processor 1025. Non-limiting examples of the codes and routines include the learning algorithm, the LOESS algorithm, the regression algorithm coupled with the outlier rejection scheme, the trending algorithm, the linear approximation algorithm, the model based pattern recognition algorithm, and the state space algorithm. In another embodiment, the memory 1030 stores one or more patterns that indicate patient distress. Non-limiting examples of the one or more patterns include a rate of decrease in $SpO_2$ with criterions for compensatory hyperventilation that indicates the Type-I respiratory distress, a rate of decrease in minute ventilation and $SpO_2$ that indicates Type-II respiratory distress, and a rate of increase in heart rate combined with a rate of decrease in blood pressure that indicates ventricular tachycardia. In one embodiment, the distress detector 1020 learns the one or more patterns based on a learning algorithm using previously generated clinical data. In another embodiment, the distress detector 1020 receives the one or more patterns from the user terminal 1040 based on a user input received from a user of the distress detector 1020, for example, a nurse, a patient, an administrator, and the like.

The user terminal 1040 may be any device that is configured to receive the user input from the user and transmit it to the distress detector 1020. The user terminal 1040 is further configured to receive a notification from the distress detector 1020 and provide the notification to the user.

Non-limiting examples of the user terminal 1040 include the television 771, the health monitor 772, a mobile phone, such as the iPhone 773, a touch screen, the laptop 774, the portable electronics 775, and the nurse station 734 as illustrated in the embodiment of FIG. 7. The user terminal 1040 includes a display device 1050 for displaying one or more user interfaces for receiving the user input and providing the notification to the user. Non-limiting examples of the user input include a time period for receiving the plurality of patient data, the one or more patterns in the plurality of patient data that indicate patient distress, one or more conditions for triggering an alarm, and a format (e.g., a color coding scheme, a type of graph, and the like) for receiving the notification in the event of patient distress. Non-limiting examples of the notification include a graph and a text message indicating the patient distress.

FIG. 11 illustrates a flow chart of an exemplary method 1100 for identification of patient distress, in accordance with aspects of the present specification. FIG. 11 is described with reference to the components of FIG. 10. At step 1102, the distress detector 1020 receives a first patient data and a second patient data for a time period, where the first patient data and the second patient data are contemporaneously measured from a patient. For example, the distress detector 1020 receives a heart rate and a blood pressure that are contemporaneously measured from a patient by the plurality of sensors 1010. Further, at step 1104, the distress detector 1020 identifies a plurality of segmented trends in the first patient data and the second patient data as one of an uptrend, a downtrend, and neutral. In one example, the distress detector 1020 identifies a plurality of segmented trends in the heart rate and the blood pressure of the patient based on, for example, a trending algorithm, a piecewise linear approximation algorithm, and the like.

Furthermore, at step 1106, the distress detector 1020 classifies at least one segmented trend from the plurality of segmented trends as a pattern. In one example, the distress detector 1020 classifies one or more segmented trends within a time frame of the received heart rate data that match or exceed a rate of increase in heart rate as a pattern that indicates patient distress. In such an example, the time frame and the rate of increase in heart rate may defined and stored in the memory 1030 by a nurse using the user terminal 1040. In another example, the distress detector 1020 correlates and classifies a first subset of segmented trends associated with the received heart rate and a second subset of segmented trends associated with the received blood pressure as a pattern indicating ventricular tachycardia (i.e., patient distress). In such an example, the first subset of segmented trends show an increase of heart rate within a time frame and the second subset of segmented trends show a decrease of blood pressure within the same time frame. In either example, the distress detector 1020 classifies at least one segmented trend from the plurality of segmented trends as a pattern based on, for example, a state space algorithm, a model based pattern recognition algorithm, and the like.

Subsequently, at step 1108, the distress detector 1020 triggers an alarm as an early warning of patient distress based on the pattern. In one example, the distress detector 1020 triggers an alarm (not shown) coupled with the user terminal 1040 in response to classifying at least one segmented trend as a pattern that indicates patient distress. In one embodiment, the distress detector 1020 triggers an alarm if the pattern satisfies the one or more conditions for triggering an alarm. The one or more conditions may be provided by the user of the distress detector 1020.

In one embodiment, the distress detector 1020 may prevent triggering false alarms based on the pattern. In one example, the first subset of segmented trends shows an increase of heart rate within a time frame and the second subset of segmented trends shows a flat trend (i.e., neutral) in blood pressure within the same time frame. In such an example, the distress detector 1020 classifies the first and the second subset of segmented trends as a pattern that indicates that the patient is not in distress. Thus, even though the heart rate of the patient increases, the distress detector 1020 advantageously prevents the triggering of the alarm since the patient is not in distress. In a further embodiment, the distress detector 1020 generates graphical data for providing a notification to a user of the distress detector 1020. The notification may include, text, a graph including the plurality of segmented trends, and the like. In one example, the plurality of segmented trends and the patient data may be highlighted based on a color coding scheme provided by the user. In such an embodiment, the distress detector 1020 may transmit the graphical data to the user terminal 1040. The display device 1050 may then render the graphical data and provide the notification to the user.

FIG. 12 illustrates a pictorial representation of a graph 1200 illustrating the blood pressure 1210 and the heart rate 1230 of a patient in accordance with aspects of the present specification. FIG. 11 is described with reference to the components of FIG. 10. In the illustrated embodiment, the blood pressure 1210 and the heart rate 1230 may be measured contemporaneously from the patient by the plurality of sensors 1010. The distress detector 1020 identifies a plurality of segmented trends 1220*a*, 1220*b*, 1220*c*, . . . , 1220*n*, 1240*a*, 1240*b*, 1240*c*, 1240*d*, . . . , 1240*n* in the blood pressure 1210 and the heart rate 1230 based on, for example, a piecewise linear approximation algorithm. For example, the distress detector 1020 identifies the section of the blood pressure 1210 between 20-25 seconds as a downtrend 1220*a*. Similarly, the distress detector 1020 identifies the section of the heart rate 1230 between 12-35 seconds as neutral 1240*a*. Similarly, the distress detector 1020 identifies the section of the heart rate 1030 between 70-72 seconds as an uptrend 1240*d*.

In the illustrated embodiment, the distress detector 1020 determines that the section of the blood pressure 1210 within the time frame of 37-50 seconds decreases and the section of the heart rate 1230 with the same time frame increases. Thus, the distress detector 1020 correlates the subset of segmented trends 1220*b*, 1220*c* associated with the blood pressure 1210 and the subset of segmented trends 1240*b*, 1240*c* and classifies them as a pattern indicating ventricular tachycardia (i.e., patient distress). The distress detector may then trigger an alarm in real-time as a warning for ventricular tachycardia. Further, the distress detector 1020 determines that section of the heart rate 1230 within the time frame of 70-80 seconds increases and the section of the section of the blood pressure 1210 within the same time frame remains unchanged. Thus, the distress detector 1020 classifies the segmented trends 1220*n*, 1240*d* and 1240*n* as a pattern that indicates that the patient is not in distress and prevents triggering a false alarm. Although in the illustrated embodiment, the distress detector 1020 classifies the segmented trends 1220*b*, 1220*c*, 1240*b*, and 1240*c* as a pattern indicating ventricular tachycardia, in another embodiment, the distress detector 1020 may classify the segmented trends 1220*b*, 1220*c*, 1240*b*, and 1240*c* as a pattern indicating shock.

In a further embodiment, the distress detector 1020 may generate and transmit a notification that comprises the blood pressure 1210 and the heart rate 1230 based on a color coding scheme provided as user input. In such an embodiment, the section of the blood pressure 1210 and the heart rate 1230 within a time frame of 37-50 seconds may be represented in red. Further the section of the blood pressure 1210 and the heart rate 1230 within a time frame of 70-80 seconds may be represented in black. The remaining sections of the blood pressure 1210 and the heart rate 1230 may be represented in blue. The notification may be rendered and displayed by the display device 1050 to, for example, a nurse tending to the patient.

Having thus described several exemplary embodiments of the invention, it is to be appreciated various alterations, modifications, and improvements will readily occur to those skilled in the art. For example, in some embodiments, such alterations, modifications, and improvements are intended to be part of this disclosure, and are intended to be within the scope of the invention. Accordingly, the foregoing description and drawings are by way of example only.

What is claimed as new and desired to be protected by Letters Patent of the United States is:

1. A method, comprising:
   receiving, with at least one processor, a first patient data related to a first physiological parameter and a second patient data related to a second physiological parameter for a time period, wherein the first patient data and the second patient data are measured from a patient and wherein the first patient data comprises a heart rate of the anent and the second patient data comprises a blood pressure of the patient;
   identifying, with the at least one processor, a plurality of segmented trends comprising a first subset of segmented trends based on the first patient data and a second subset of segmented trends based on the second patient data, wherein the first patient data comprises a heart rate of the patient and the second patient data comprises a blood pressure of the patient and wherein each of the plurality of segmented trends is classified as one of an uptrend, a downtrend, and neutral trend;
   correlating the first subset of segmented trends with the second subset of segmented trends to determine a correlated first and second subsets of segmented trends;
   classifying, with the at least one processor, the correlated first and second subsets of segmented trends as one of a plurality of patterns, wherein each of the plurality of patterns is representative of warning of patient distress based on a state space model characterized by a Hidden Markov Model framework, using a Viterbi algorithm and wherein the patient distress consists of ventricular tachycardia or shock; and
   triggering, with the at least one processor, an alarm when the at least one processor classifies the correlated first and second subsets as one of the plurality of patterns.

2. The method of claim 1, wherein identifying the plurality of segmented trends in the first patient data and the second patient data is based on a piecewise linear approximation algorithm.

3. The method of claim 1, wherein classifying the subset of the plurality of segmented trends as a pattern is based on a model based pattern recognition algorithm.

4. A system, comprising:
   a plurality of sensors configured to measure a first patient data related to a first patient physiological parameter and a second patient data related to a second physiological parameter from a patient for a time period and wherein the first patient data comprises a heart rate of the patient and the second patient data comprises a blood pressure of the patient; and
   a distress detector communicatively coupled to the plurality of sensors and configured to:
      identify a plurality of segmented trends comprising a first subset of segmented trends based on the First patient data and a second subset of segmented trends based on the second patient data, wherein the first patient data corn rises a heart rate of the patient and the second patient data comprises a blood pressure of the patient;
      classify each of the plurality of segmented trends of both the first subset and the second subset as one of an uptrend, a downtrend, and neutral trend;
      correlate the first subset of segmented trends with the second subset of segmented trends to determine a correlated first and second subsets of segmented trends:
      classify the correlated first and second subsets of segmented trends as one of a plurality of patterns, wherein each of the plurality of patters is representative of a warning of patient distress consisting of ventricular tachycardia or shock based on a state space model characterized by a Hidden Markov Model framework, using a Viterbi algorithm; and
      trigger an alarm when the at least one processor classifies the correlated first and second subsets as one of the plurality of patterns.

5. The system of claim 4, wherein the distress detector is configured to identify the plurality of segmented trends in the first patient data and the second patient data based on a piecewise linear approximation algorithm.

6. The system of claim 4, further comprising a user terminal configured to receive user input, wherein the user input comprises the lime period, the pattern, and one or more conditions for triggering the alarm.

* * * * *